(12) United States Patent
Thomas et al.

(10) Patent No.: US 11,918,678 B2
(45) Date of Patent: Mar. 5, 2024

(54) HAIR CLEANSING COMPOSITION

(71) Applicant: Conopco, Inc., Englewood Cliffs, NJ (US)

(72) Inventors: Matthew Rhys Thomas, Wirral (GB); Jeremy Robert Westwell, Tarporley (GB); Sally Elizabeth Wood, Warrington (GB); Sophia Isabel Alice Quenby-Ma, Liverpool (GB)

(73) Assignee: Conopco, Inc., Englewood Cliffs, NJ (US)

( * ) Notice: Subject to any disclaimer, the term of this patent is extended or adjusted under 35 U.S.C. 154(b) by 544 days.

(21) Appl. No.: 17/263,987

(22) PCT Filed: Jul. 23, 2019

(86) PCT No.: PCT/EP2019/069854
§ 371 (c)(1),
(2) Date: Jan. 28, 2021

(87) PCT Pub. No.: WO2020/025404
PCT Pub. Date: Feb. 6, 2020

(65) Prior Publication Data
US 2021/0299025 A1    Sep. 30, 2021

(30) Foreign Application Priority Data
Jul. 30, 2018  (EP) .................... 18186422

(51) Int. Cl.
| A61K 8/00 | (2006.01) |
| A61K 8/04 | (2006.01) |
| A61K 8/34 | (2006.01) |
| A61K 8/44 | (2006.01) |
| A61K 8/46 | (2006.01) |
| A61K 8/60 | (2006.01) |
| A61K 8/73 | (2006.01) |
| A61Q 5/02 | (2006.01) |

(52) U.S. Cl.
CPC .............. *A61K 8/731* (2013.01); *A61K 8/044* (2013.01); *A61K 8/345* (2013.01); *A61K 8/442* (2013.01); *A61K 8/463* (2013.01); *A61K 8/60* (2013.01); *A61Q 5/02* (2013.01); *A61K 2800/412* (2013.01); *A61K 2800/805* (2013.01)

(58) Field of Classification Search
None
See application file for complete search history.

(56) References Cited

U.S. PATENT DOCUMENTS

| 3,958,581 | A | 5/1976 | Abegg et al. |
| 3,962,418 | A | 8/1976 | Birkofer |
| 4,009,256 | A | 2/1977 | Nowak, Jr. et al. |
| 2001/0004869 | A1 | 6/2001 | Cantiani et al. |
| 2012/0100092 | A1 | 4/2012 | Murray |
| 2019/0053528 | A1* | 2/2019 | Goudappel ............ C11D 3/382 |

FOREIGN PATENT DOCUMENTS

| CN | 1280486 | 1/2001 |
| CN | 107920563 | 4/2018 |
| CN | 108130215 | 6/2018 |
| EP | 0530974 | 3/1993 |
| EP | 2196186 | 6/2010 |
| WO | WO9522311 | 8/1995 |
| WO | WO9631188 | 10/1996 |
| WO | WO9920241 | 4/1999 |
| WO | WO2004052324 | 6/2004 |
| WO | WO2014017913 | 1/2014 |
| WO | WO2016075370 | 5/2016 |
| WO | WO2016107793 | 7/2016 |
| WO | WO2017009042 | 1/2017 |
| WO | WO2017019752 | 2/2017 |
| WO | WO2017174260 | 10/2017 |

OTHER PUBLICATIONS

Search Report and Written Opinion in EP18186422; dated Mar. 22, 2019; European Patent Office (EPO).
Search Report and Written Opinion in PCTEP2019069854; dated Dec. 16, 2019.

* cited by examiner

*Primary Examiner* — Necholus Ogden, Jr.
(74) *Attorney, Agent, or Firm* — Carter, DeLuca & Farrell LLP; George Likourezos; Bret P. Shapiro

(57) ABSTRACT

Hair care cleansing composition comprising—a) from 1 to 50 wt % of a cleansing surfactant selected from the group consisting of anionic surfactant, zwitterionic or amphoteric surfactant, non-ionic and mixtures thereof; and b) from 0.01 to 3 wt %, by weight of the total composition, of defibrillated primary cell wall material comprising cellulose microfibrils, wherein • the defibrillated primary cell wall material comprises up to 20 wt. % of water, based on the total weight of the fibrils; and wherein • the cellulose has an average degree of crystallinity of less than 50%, and wherein • the defibrillated primary cell wall material comprises polyols distributed between the fibrils.

19 Claims, No Drawings

HAIR CLEANSING COMPOSITION

CROSS REFERENCE TO RELATED APPLICATIONS

The present application is a U.S. National Phase Application under 35 U.S.C. § 371 of International Application No. PCT/EP2019/069854, filed on Jul. 23, 2019, which claims priority to European patent application No. 18186422.4 filed on Jul. 30, 2018, the contents of which are incorporated herein in their entireties.

TECHNICAL FIELD

The invention relates to a hair cleansing composition comprising defibrillated primary cell wall material comprising cellulose microfibrils, wherein the cellulose has a degree of crystallinity of less than 50%.

BACKGROUND

The primary cell walls of plants comprise cellulose microfibrils, hemicellulose and pectin. In native primary cell walls the cellulose microfibrils are tethered by the hemicellulose and bound in the pectin matrix to form a rigid 2D structure. Primary cell wall material is widely available, also on industrial scale, in the form of waste streams, e.g. from the citrus processing industry. It is known that such primary cell wall material, optionally after de-pectinizing, can undergo defibrillation (also known as activation) by high shear treatment. An example is high-pressure homogenization in the presence of an aqueous medium. In the defibrillated primary cell wall material the cellulose fibrils are disentangled and rearranged from the mostly 2D structure into a more 3D structure. As a result, the surface area of the primary cell wall material is expanded and with the greater surface area provides improved functionality or structuring to the aqueous media. When used in products as part of an aqueous-phase this allows for improved high temperature (eg 45-50° C.) stability, suspension of benefit particles (eg silicone droplets, anti-dandruff agents, micas or fragrance encaps) and/or foam stability of the products in which they are present.

The cellulose degree of crystallinity is characteristic for the source of material used. For example, bacterial cellulose or wood pulp cellulose (i.e. or paper-pulp cellulose) has a degree of crystallinity of greater than 50%. The cellulose derived from the primary cell walls of non-wood plant parts, (e.g. citrus fruits) has a crystallinity of 50% or less.

For reasons of reducing bulk and energy for transport, it is desirable to provide defibrillated primary cell wall material in dry form. However once dried such compositions again need very high shear treatment to fully recover the structuring properties in aqueous media. This is undesirable as high-shear equipment increases cost and energy input to manufacture products using the dry defibrillated primary cell wall material. Furthermore, this may also limit its applicability to products comprising shear sensitive ingredients. For example, many hair care products contain encapsulated materials, which can be sensitive to high-shear treatment.

US2001/0004869 A1 describes the use of co-additives, homogenized together with the nanofibrils (microfibrils), to provide a composition in dry form, which can be more readily dispersed in water. In particular it describes the use of one or more co-additives chosen from carboxymethyl cellulose with a degree of substitution of up to 0.95, saccharide monomers or oligomers, certain compounds of the formula $(R_1R_2N)COA$ and/or cationic or amphoteric surfactants. In the first place the required used of carboxymethyl cellulose is undesirable as it is a chemically modified form of cellulose, which reduced consumer acceptance for the products comprising it. Secondly, it was observed that when using such co-additives the functionality of the cellulose nanofibril composition in dry form leaves to be desired as incomplete recovery of the functional properties was observed, in particular when low-shear mixing is used.

WO 2017/019752 discloses citrus fibers in dry form having a storage modulus (G') of at least 50 Pa, said G' being measured on an aqueous medium containing an amount of 2 wt % citrus fibres dispersed therein under a low-shear stirring of less than 10000 rpm. The citrus fibres may be included in a composition comprising a surfactant system.

To clarify, it is not that dispersibility in water is the issue of the defibrillated primary cell wall material in dry form, but rather the recovery of the functional properties imparted by the defibrillated cell wall material to an aqueous medium. This is believed due to the fact that upon drying the defibrillated material forms clumps which as such can be readily dispersed, but to recover the original functional properties, the clumps themselves require further disruption and de-agglomeration, requiring high shear.

It is an object of the present invention to provide a composition comprising dry defibrillated primary cell wall material comprising cellulose microfibrils, wherein the cellulose has a degree of crystallinity of less than 50%, which can provide improved structuring to liquid media, preferably aqueous media, under low-shear mixing.

Furthermore, in view of improved consumer acceptance of short ingredient lists, it is desirable that the solution involves no further ingredients other than those already found in the products of which a liquid medium is structured by the defibrillated primary cell wall material. This is particularly the case for regularly used (daily/weekly) home and personal cleaning products.

SUMMARY OF THE INVENTION

Accordingly, in a first aspect, the present invention provides a hair cleansing composition comprising
 a) from 1 to 50 wt % of a cleansing surfactant selected from the group consisting of anionic surfactant, zwitterionic or amphoteric surfactant, non-ionic and mixtures thereof; and
 b) from 0.01 to 3 wt %, by weight of the total composition, (preferably 0.02 to 2, more preferably 0.05 to 1.5 wt %) of defibrillated primary cell wall material comprising cellulose microfibrils, wherein
  the defibrillated primary cell wall material comprises up to 20 wt. % of water, based on the total weight of the fibrils; and wherein
  the cellulose has an average degree of crystallinity of less than 50%, and wherein
  the defibrillated primary cell wall material comprises polyol distributed between the fibrils.

In a second aspect of the invention there is provided is a method of cleansing comprising the step of applying to the hair a hair cleansing composition of the first aspect.

In a third aspect, the invention provides a process for the manufacture of a composition according to the first aspect, comprising the steps of:

a) providing a defibrillated primary cell wall material comprising cellulose microfibrils, wherein
   the defibrillated primary cell wall material comprises up to 20 wt. % of water, based on the total weight of the fibrils; and wherein
   the cellulose has an average degree of crystallinity of less than 50%, and wherein the defibrillated primary cell wall material comprises polyol distributed between the fibrils;
b) providing further ingredients comprising at least a water-phase and from 1 to 50 wt % of a cleansing surfactant selected from the group consisting of anionic surfactant, zwitterionic or amphoteric surfactant, non-ionic and mixtures thereof;
c) mixing the ingredients provided at step a) and b) under low shear to provide a cleaning product, where low-shear means using a rotor stator type mixer or dispersion disc type mixer with a rotor or disc tip speed of less than 40 m/s, preferably of from 5 to 35 m/s, more preferably of from 10-30 m/s.

An advantage of this material is that it can be dried down with the polyol. The resulting dry fibre is then more easily redispersed using a relatively low shear to deliver it's full structuring capability.

Polyols distributed between the fibrils improve the recovery of defibrillated fibrils comprising up to 20 wt. % of water, based on the total weight of the fibrils, upon mixing with a water-phase. This allows improved structuring upon low shear mixing with a water-phase. This allows the process for the manufacture of a structured liquid composition to use low-shear equipment, which therefore is much more efficient.

DETAILED DESCRIPTION

Any feature of a particular embodiment of the present invention may be utilised in any other embodiment of the invention. The word "comprising" is intended to mean "including" but not necessarily "consisting of" or "composed of". In other words, the listed steps or options need not be exhaustive. It is noted that the examples given in the description below are intended to clarify the invention and are not intended to limit the invention to those examples per se. All weight percentages (wt. %) are based on the final weight of the composition unless otherwise indicated. Similarly, all volume percentages (vol. %) are based on the final volume of the composition unless otherwise indicated. Except in the examples and comparative experiments, or where otherwise explicitly indicated, all numbers in this description indicating amounts of material or conditions of reaction, physical properties of materials and/or use are to be understood as modified by the word "about". Unless specified otherwise, numerical ranges expressed in the format "from x to y" are understood to include x and y. When for a specific feature multiple preferred ranges are described in the format "from x to y", it is understood that all ranges combining the different endpoints are also contemplated. For the purpose of the invention ambient (or room) temperature is defined as a temperature of about 20 degrees Celsius.

Composition

Preferably the defibrillated primary cell wall material comprises up to 15 wt. %, more preferably up to 12 wt. %, even more preferably up to 10 wt. % and still even more preferably up to 8 wt. % of water, based on the total weight of the fibrils.

As such the defibrillated primary cell wall material may optionally comprise (e.g. encapsulated) water as long as it remains sufficiently dry. Preferably the defibrillated primary cell wall material of the composition according to the invention comprises up to 20 wt. %, preferably up to 15 wt. %, more preferably up to 12 wt. %, even more preferably up to 10 wt. % and still even more preferably up to 8 wt. % of water, preferably as based on the total weight of the fibrils, for example 0.01 to 20 wt. %, preferably 0.01 to 15 wt. %, more preferably 0.01 to 12 wt. %, even more preferably 0.01 to 10 wt. % and still even more preferably 0.01 to 8 wt. % of water, preferably as based on the total weight of the fibrils.

Primary Cell Wall Material

In general, primary cell wall material typically contains cellulose microfibrils, hemicellulose, pectin and in many cases lignin. This contrasts with the cell walls of fungi (which are made of chitin), and of bacteria, which are made of peptidoglycan. Primary plant cell walls contain lignin only in minor amounts, if at all. The primary cell wall material according to the invention may comprise some lignin, preferably up to 10 wt. %, calculated on total amount of cell wall material, and more preferably does not contain substantial amounts of lignified tissue. Even more preferably the primary cell wall material consists essentially of non-lignified tissue as understood by the skilled person in the area of plant biology. Preferably at least 50 wt. %, more preferably at least 75 wt. %, even more preferably at least 90 wt. % of the primary cell wall material is derived from plant parenchymal tissue. The source of the plant parenchyma cells may be any plant that contains plant parenchyma cells having a cellulose skeleton.

Preferably the primary cell wall material comprises primary cell wall material derived from (preferably the parenchymal tissue of) fruits, roots, bulbs, tubers, seeds, leaves and combinations thereof; more preferably is derived from citrus fruit, tomato fruit, peach fruit, pumpkin fruit, kiwi fruit, apple fruit, mango fruit, sugar beet, beet root, turnip, parsnip, maize, oat, wheat, peas and combinations thereof; and even more preferably is derived from citrus fruit, tomato fruit and combinations thereof. The most preferred source of primary cell wall material is from (preferably the parenchymal tissue of) citrus fruit. The citrus family is a large and diverse family of flowering plants. Common varieties of the citrus fruit include oranges, sweet oranges, clementines, kumquats, tangerines, tangelos, satsumas, mandarins, grapefruits, citrons, pomelos, lemons, rough lemons, limes and leech limes.

The primary cell wall material preferably has undergone several pre-treatment steps before it is defibrillated. Such pre-treatments preferably comprise one or more steps of heating, cooking, washing, refining, depectinating; and more preferably comprise the steps of washing and/or depectinating. Preferably the "primary cell wall material" is primary cell wall material from which most (i.e. more than 50 wt. %) of all water-soluble components, and preferably essentially all, water soluble components have been removed. Water-soluble components being components, which can be removed by washing with water at a temperature of 20 degrees Celsius. Preferably the source of primary cell wall material is in the form of a washed paste or pulp. Such are commercially available from Herbafood (Citrus fiber AQ+N).

Plant cell walls, especially in parenchymal tissue contain hemicelluloses and pectin in addition to cellulose microfibrils. However, the primary cell wall material of the invention need not contain hemicellulose and/or pectin. The hemicellulose may have been (partly) removed when the primary cell wall material is prepared/pre-treated. Preferably the primary cell wall material comprises up to 40 wt. %, more preferably up to 30 wt. %, even more preferably up to 20 wt. % and still even more preferably up to 5 wt. % of hemicelluloses, based on the total dry weight of the primary cell wall material. Likewise, the pectin may have been (partly) removed when the primary cell wall material prepared/pre-treated. Preferably the primary cell wall material comprises up to 30 wt. %, more preferably up to 25 wt. %, even more preferably up to 20 wt. % and still even more preferably up to 5 wt. % of pectin, based on the total dry weight of the primary cell wall material.

Cellulose Microfibrils

Cellulose microfibrils are well-known in the art. A typical microfibril generally comprises 20 to 50 aligned beta-1-4-glucose polymer chains. In native primary cell wall material, cellulose microfibrils can be (partly) present in the form of aggregates building the cell wall.

Preferably the primary cell wall material according to the invention comprises at least 50 wt. %, more preferably at least 60 wt. %, even more preferably at least 70 wt. %, still more preferably at least 80 wt. % and still even more preferably at least 90 wt. % of cellulose microfibrils, based on total the dry weight of the primary cell wall material. Still even more preferably the primary cell wall material consists essentially of cellulose microfibrils.

The weight percentage of cellulose microfibrils in the primary cell wall material preferably is increased by removing soluble and unbound sugars, protein, polysaccharides, oil soluble oils, waxes and phytochemicals (e.g. carotenoids, lycopene). This is suitably achieved using well-known techniques including cutting up the cell wall material, cooking, washing, centrifugation, decanting and drying as is well-known to the skilled person.

The composition of the invention comprises defibrillated cell wall material, i.e. the cellulose microfibrils that are present in the primary cell wall are at least partially disentangled, preferably without substantially breaking them. Preferably the average length of the cellulose microfibrils in the defibrillated primary cell wall material is more than 1 micrometer and preferably more than 5 micrometers. Preferably at least 80 wt. % of the cellulose microfibrils is smaller than 50 nm in diameter, more preferably is smaller than 40 nm in diameter, even more preferably is smaller than 30 nm, still even more preferably is smaller than 20 nm and still even more preferably is smaller than 10 nm. The microfibril diameter is determined using the following method using transmission electron microscopy (TEM) according to (D. Harris et. al. Tools for Cellulose Analysis in Plant Cell Walls Plant Physiology, 2010(153), 420). In particular, a dispersion of plant source rich in primary cell wall material is diluted in distilled water resulting in a thin layer. These dispersions are then imaged on a Carbon only 300 mesh Copper TEM grid (Agar Scientific) using a Tecnai 20 Transmission electron microscope (FEI Company) operated at a voltage of 200 kV. To enhance image contrast between individual microfibrils, a 2% phosphotungstic acid solution at pH 5.2 is used as a negative stain. To do this the fiber-loaded TEM grids are incubated with 2% phosphotungstic acid and air-dried after removal of the excess of fluid.

The cellulose microfibrils according to the invention preferably have an average degree of crystallinity of less than 50%. Preferably the average degree of crystallinity of the cellulose in the microfibrils is up to 40%, more preferably up to 35% and even more preferably up to 30%.

Table 1 shows the average degree of crystallinity of typical sources of cellulose microfibrils. It shows that the cellulose in primary cell wall material sourced from plant parenchymal tissue typically has a degree of crystallinity of less than 50 wt. %.

TABLE 1

Average degree of crystallinity of cellulose (all polymorph cellulose I).

| Source | Average degree of crystallinity (%) |
| --- | --- |
| Tomato fibers | 32 |
| Citrus fiber (Citrus Fiber AQ + N) | 29 |
| Nata de Coco | 74 |
| Cotton | 72 |
| Wood pulp fiber (Meadwestvaco) | 61 |
| Sugar beet fibre (Nordix Fibrex) | 21 |
| Pea fibres (PF200vitacel) | 42 |
| Oat fibres (780 Sunopta) | 43 |
| Corn hull (Z-trim) | 48 |
| Sugar cane Fiber (Ultracel) | 49 |

The average degree of crystallinity is measured according to the following method using wide angle X-ray scattering (WAXS) with the following protocol. The measurements are performed on a Bruker D8 Discover X-ray diffractometer with GADDS (General Area Detector Diffraction System) (From Bruker-AXS, Delft, NL) (Part No: 882-014900 Serial No: 02-826) in a theta/theta configuration. A copper anode is used, and the K-alpha radiation with wavelength 0.15418 nm is selected. The used instrumental parameters are shown in table 2.

TABLE 2

D8 Discover instrumental parameters for WAXS measurements.

| | $2\theta$ (9-42°) |
| --- | --- |
| Theta 1 | 10.000 |
| Theta 2 | 10.000/25.000 |
| Detector Bias (kV/mA) | 40/40 |
| Time (sec) | 300 |
| Collimator (mm) | 0.3 |
| Detector distance (cm) | 25 |
| Tube Anode | Cu |

The average degree of crystallinity (Xc) is calculated from the following equation:

$$Xc(\%) = \frac{\text{Area crystalline phase}}{\text{Area crystalline} + \text{amorphous phase}} * 100\%$$

The areas of the diffraction lines of the crystalline phase are separated from the area of the amorphous phase by using the Bruker EVA software (version 12.0).

Preferably the fibres are defibrillated citrus fibre with no intact cells walls present. Preferred materials from which the defibrillated citrus fibers are derived, are selected from citrus whole peel, (fully or partially) depectinased citrus peel, or commercially available dry or slurry fibers. Preferred fibers are those citrus peel derived fibers that have the physical properties of: 100% self suspending of 0.3% solids in 0-0.1 L water at room temperature, and a G' plateau value at 0.3% solids of 1-5 Pa, a G' plateau value at 1.7% solids of 800-1500 Pa.

In a preferred embodiment, the fibres are activated citrus fibers having the following characteristics:
(i) a self-suspending capacity (determined, in the presence of glycerol, at 0.1 wt % dry fibre upon dispersion at 8000 rpm for 10 minutes) of 45-58%, and
(ii) a G' (determined in the presence of the glycerol, at 2.0 wt % dry fibre dispersed at 8000 rpm for 10 minutes and between 10-40 wt % glycerol) of between 600-1200 Pa;
wherein the determinations in (i) and (ii) above are carried out as specified in patent application no. EP15178987.2.

Polyols

Polyols are alcohols comprising multiple (i.e. more than one) hydroxyl group. The polyols may be monomeric or polymeric polyols. Preferably the polyols are monomeric.

For example, the sugar alcohols, such as sorbitol or sucrose. Preferably the polyol has a molecular weight of up to 400 MW and more preferably is selected from glycerol, diglycerol, monopropylene glycol, dipropylene glycol, ethylene glycol and polyethylene glycol, sorbitol, sucrose and mixtures thereof, most preferably selected from glycerol, sorbitol, sucrose and mixtures thereof. Even more preferred polyethylene glycols are diethylene glycol and triethylene glycol.

Preferably the polyols comprise from 2 to 50, more preferably from 2 to 20, even more preferably from 2 to 10, still even more preferably from 2 to 5 and still even more preferably 2 hydroxyl groups.

Polyol is distributed between the fibrils used in the cleansing compositions of the present invention. Additional polyol is also optionally present in the composition.

In a preferred embodiment, the polyol distributed between the fibrils used in the present invention is glycerol that is most preferably present in an amount of from 10 to 40 wt %, based on the weight of the total dry-weight of the fibrils.

In particular it was observed that use of polyols at a level of at least 15 wt. %, based on the total dry-weight of the fibrils provided further improved recovery of the structuring capacity.

By "distributed between the fibrils" is herein understood that the polyols are in contact with at least part of the cellulose microfibril surface area. It was surprisingly observed that the presence of said polyols distributed between the fibrils reduces the energy/shear requirement for the defibrillated material comprising up to 20 wt. % of water, based on the total dry-weight of the fibrils, to recover its structuring capacity upon mixing with an aqueous medium.

Preferably the total amount of polyols (including the polyol distributed between the fibres and any optional additional polyol) in the hair cleansing composition is at least 10 wt. %, based on the dry-weight of the primary cell wall material in the final composition according to the invention, more preferably 15 to 1000 wt %, even more preferably is from 20 to 500 wt. %, Preferably the amount of polyols added to the cleansing composition, inclusive of polyols resulting from the addition of the composition according to the invention and from additional polyols added directly to the cleansing composition, is at least 0.001%, preferably from 0.0015% to 10%, more preferably is from 0.002% to 5 wt. %, by wt of the total cleansing composition.

The amount of polyol present distributed between the fibrils is suitably present in an amount of 0.001 to 0.05 wt %, by weight of the total composition and any optional additional polyol, which is not distributed within the fibrils, is suitably present at 0.15 to 10 wt %, preferably 0.25 to 5 wt %, most preferably 0.5 to 3 wt % by weight of the total composition.

The polyols according to the invention are preferably water-soluble. This allows for improved distribution between the fibrils leading to improved recovery of the structuring capacity. More preferably they are water-soluble at a concentration of 0.2 wt. %, even more preferably at a concentration of 0.5 wt. %, still even more preferably at a concentration of 1.0 wt. % and still even more preferably at a concentration of 2.0 wt. % when measured in (pure) water at ambient conditions.

Method to Manufacture the Composition

At step a) of the process to manufacture the composition according to the invention, the primary cell wall material comprising cellulose microfibrils is defibrillated by subjecting it to sufficient mechanical energy (e.g. shear). The source of primary cell wall material preferably is non-defibrillated, however already defibrillated material can suitable be used (and converted to a composition according to the invention comprising polyols distributed between the fibrils). Non-defibrillated primary cell wall material as such and without the presence of polyols distributed between the fibrils is commercially available, for example as fruit and vegetable purees, Herbacel AQ Plus citrus fibre (Supplier: Herbafoods).

Suitable defibrillation techniques are known in the art. Defibrillation is preferably carried out using high shear treatment, pressure homogenization, cavitation, explosion, pressure increase and pressure drop treatments, colloidal milling, intensive blending, extrusion, ultrasonic treatment, extrusion, grinding, and combinations thereof and more preferably by pressure homogenization treatment. Preferred homogenizers include high-pressure homogenizers manufactured by GEA Niro Soavi of Parma (Italy), such as the NS Series, or the homogenizers of the Gaulin and Rannie series manufactured by APV Corporation of Everett, Mass. (US). Preferred pressures when using high-pressure homogenizers are from 500 bar to 2000 bar, more preferably between 600 bar and 1000 bar. Preferably extrusion, grinding or a combination thereof is used to defibrillate primary cell wall material comprising cellulose microfibrils at higher concentration of from 5 to 50 wt. %.

The defibrillation is performed in the presence of an aqueous medium. Preferably the aqueous medium comprises at least 50 wt. %, more preferably at least 75 wt. % and even more preferably at least 90 wt. % of water. The defibrillation can be done as part of the process for obtaining the primary cell wall material. The defibrillation treatment can be arrived at by a single or a succession of treatments. The amount of aqueous medium at step a) can vary but preferably is such that a liquid slurry is formed. Preferably at step a) the amount of aqueous medium is at least 1 times, preferably at least 5 times, more preferably from 10 to 500 times and even more preferably from 20 to 200 times the amount of primary cell wall material, wherein the latter is based on dry-weight.

At step b) the water content of the mixture obtained at step a) is reduced. Depending on other liquids present, the final composition according to the invention is in the form of a paste, cake or powder, preferably is in the form of a cake or powder and more preferably is in the form of a powder. It will be appreciated that a cake can suitably be modified into a powder by appropriate milling. Preferably the powder is a free-flowing powder. The reducing of water at step b) can be done using techniques known in the art. Preferably the amount of water is reduced using evaporation and/or filtration.

In a preferred method to manufacture the composition according to the invention after step a) and before step b) the defibrillated primary cell wall material in aqueous medium is contacted with an organic solvent to obtain a precipitate phase and a liquid phase, followed by separating said precipitate phase from the liquid phase to obtain a semi-dry cake of the defibrillated primary cell wall material having a dry substance-content of at least 10 wt. % relative to the mass of said cake. The cake may subsequently be further treated in step b) as the mixture. Said preferred precipitation step further improves the capacity of the composition the recover and structure a water-phase.

Preferably the polyols are added at step a).

Preferably e.g. for the manufacture of an instant cleaning product composition optional further ingredients are added after step b).

Process for the Manufacture of the Cleansing Product—Step a)

The invention further relates to use of the composition according to the invention to manufacture a hair cleaning composition comprising a water-phase, which allows use of low-shear mixing step.

Preferably the amount of the composition according to the invention added at step a) of the process to manufacture the cleansing product, is from 0.01 to 7.5 wt. %, based on the dry weight of the defibrillated primary cell wall material comprising cellulose microfibrils comprised by the composition. The amount of defibrillated cell wall material is suitably selected to obtain the desired effect and depends on the overall product format. More preferably, the amount of the composition added is from 0.02 to 5 wt. %, even more preferably from 0.05 to 4 wt. %, based on the dry weight of the defibrillated primary cell wall material comprising cellulose microfibrils comprised by the composition.

Preferably the total amount of water-phase provided at step a) is from 0.5 to 98 wt. %, more preferably from 1 to 95 wt. %, even more preferably from 2.5 to 90 wt. %, based on the total weight of the cleansing product.

The inclusion level of the composition according to the invention in the final hair cleansing composition comprises from 0.01 to 3 wt. %, more preferably from 0.02 to 2 wt. % and even more preferably from 0.05 to 1.5 wt. % of defibrillated primary cell wall material comprising cellulose microfibrils, by weight of the total hair cleansing composition.

The mixing of ingredients can be done in any order and/or in parts. For example, first part of the total ingredients can be mixed and the remained mixed in subsequently. The mixing at step a) is done under low shear.

As mentioned, traditionally, exploitation of the properties of e.g. citrus fibers to prepare a cleaning product with excellent rheological properties requires the use of equipment that must be able to impart high to very high shear during the manufacture of the product. Such equipment includes high-pressure homogenizers, micro-fluidizers, extruders and ultrasonic treatment equipment. Such equipment is usually costly, and in operation uses a relatively large amount of energy and therefore preferably not used in step a) in the method to make cleansing products, and more preferably are not used at all. Therefore, at steps equivalent to a), preferably no use is made of one or more high-pressure homogenizers, micro-fluidizers, extruders, ultrasonic treatment equipment or combinations thereof.

In contrast, using the composition and method according to the invention allows the manufacture of cleansing products under low shear to obtain the same or even better rheological properties when compared to use of prior art defibrillated fibers comprising up to 20 wt. % of water (i.e. but without having polyols distributed between the fibrils) prepared under high shear. In the method of the invention, step a) is preferably performed by mixing the ingredients under what is defined here as low-shear, for example, using a rotor stator type mixer known in the art (for example, but not limited, to IKA, Ystral and Silverson supplied rotor stator mixers) or dispersion disc type mixer (for example, but not limited, to Cowles disc mixers, for example those supplied by Fryma), using a rotor or disc tip speed of less than 40 m/s, more preferably of from 5 to 35 m/s, even more preferably of from 10-30 m/s. For the purpose of clarity, it is possible to use a mixer that is capable of high shear at a low shear rate, in the method of the invention.

In the method of the invention, other materials can optionally be added before or during the low shear dispersion of the composition according to the invention.

Process for the Manufacture of a Cleansing Product—Step b)

At step b) in the process for the manufacture of a cleansing product according to the invention, further ingredients are added and blended until fully dispersed using methods known in the art.

The cleansing product according to the invention is a hair cleansing product and preferably is a hair cleansing product.

Further Ingredients

At step b) further ingredients can optionally be added. Preferably the further ingredients are as typically found in the target cleansing product, which are known to the person skilled in the art. The amount of such further ingredients are based on the final total weight if the cleansing product unless otherwise specified.

Surfactant

The hair cleansing product according to the invention comprises a cleansing surfactant. Surfactants are compounds which have hydrophilic and hydrophobic portions that act to reduce the surface tension of the aqueous solutions they are dissolved in. By cleansing surfactant is meant that the surfactant provides a detersive (i.e. cleaning effect) to personal care surfaces treated as part of a cleaning, preferably a hair, process. Hair cleansing compositions according to the invention will generally comprise one or more cleansing surfactants, which are cosmetically acceptable and suitable for topical application to the hair. The cleansing surfactant may be chosen from anionic, non-ionic, amphoteric and zwitterionic compounds and mixtures thereof.

The total amount of surfactant present is from 1 to 50 wt. %, more preferably from 2 to 25 wt. %.

Where the composition of the invention is a hair cleansing product the composition preferably comprises from 2 to 40%, more preferably from 4 to 25% of total surfactant, based on the total weight of the composition. If a surfactant mixture is used that incorporates both anionic and nonionic surfactants, then preferably the ratio of anionic surfactant to nonionic surfactant is from 1:1 to 10:1, more preferably from 2:1 to 9:1, most preferably from 3:1 to 8:1.

Hair Cleansing Compositions

The composition of the invention is a hair cleansing composition.

Preferably, the cleansing surfactant is selected from the group consisting of sodium lauryl sulphate, sodium lauryl ether sulphate (n)EO, (where n is from 1 to 3), sodium ($C_{12-13}$) pareth sulphate, ammonium lauryl sulphate, ammonium lauryl ether sulphate(n)EO, (where n is from 1 to 3), alpha olefin sulfonate (of general formula $R^1$—CH=CH—$SO_3^-M^+$, in which $R^1$ is selected from linear or branched alkyl groups having from 14 to 16 carbon atoms and mixtures thereof; and M is a solubilizing cation), lauyl taurate, cocyl taurate, sodium cocoyl isethionate, lauryl ether carboxylic acid, lauryl betaine, coco betaine, cocamidopropyl betaine, sodium cocoamphoacetate, sodium laurylamphoacetate, lauryl hydroxy sultaine, coco hydroxy sultaine, lauryl aminopropyl hydroxy sultaine, coco aminopropyl hydroxy sultaine, and mixtures thereof.

Preferably, mixtures of any of the anionic, non-ionic and amphoteric cleansing surfactants has a ratio of primary to secondary surfactant of between 1:1-10:1, more preferably 2:1-9:1 and most preferably 3:1-8:1, based on the inclusion weight of the cleansing surfactant in the hair cleansing composition.

Preferably, the hair cleansing composition of the present invention comprises from 1 to 50%, preferably from 2 to 40%, more preferably from 4 to 25% of total surfactant, based on the total weight of the composition.

Hair Cleansing Compositions

Hair cleansing compositions of the present invention are generally aqueous, i.e. they have water or an aqueous solution or a lyotropic liquid crystalline phase as their major component.

Suitably, the hair cleansing composition will comprise from 50 to 98%, preferably from 60 to 92% water by weight based on the total weight of the composition.

Hair cleansing compositions according to the invention will generally comprise one or more cleansing surfactants, which are cosmetically acceptable and suitable for topical application to the hair. The cleansing surfactant may be chosen from anionic, non-ionic, amphoteric and zwitterionic compounds and mixtures thereof.

The total amount of cleansing surfactant in a hair cleansing composition for use in the invention is generally from 1 to 50%, preferably from 2 to 40%, more preferably from 4 to 25% by total weight surfactant based on the total weight of the composition.

Non-limiting examples cleansing surfactants include anionic cleansing surfactants include; alkyl sulphates, alkyl ether sulphates, pareth sulphates, alkaryl sulphonates, alkyl olefin sulphonates, N-alkyl sarcosinates, alkyl phosphates, alkyl ether phosphates, acyl amino acid based surfactants, alkyl ether carboxylic acids, acyl taurates, acyl glutamates, alkyl glycinates and salts thereof, especially their sodium, magnesium, ammonium and mono-, di- and triethanolamine salts. The alkyl and acyl groups in the preceding list generally contain from 8 to 18, preferably from 10 to 16 carbon atoms and may be unsaturated. The alkyl ether sulphates, alkyl ether phosphates and alkyl ether carboxylic acids and salts thereof may contain from 1 to 20 ethylene oxide or propylene oxide units per molecule.

Further non-limiting examples of cleansing surfactants may include non-ionic cleansing surfactants including; aliphatic ($C_8$-$C_{18}$) primary or secondary linear or branched chain alcohols with alkylene oxides, usually ethylene oxide and generally having from 6 to 30 ethylene oxide groups. Other representative cleansing surfactants include mono- or di-alkyl alkanolamides (examples include coco mono-ethanolamide and coco mono-isopropanolamide) and alkyl polyglycosides (APGs). Suitable alkyl polyglycosides for use in the invention are commercially available and include for example those materials identified as: Plantapon 1200 and Plantapon 2000 ex BASF. Other sugar-derived surfactants, which can be included in compositions for use in the invention include the $C_{10}$-$C_{18}$ N-alkyl ($C_1$-$C_6$) polyhydroxy fatty acid amides, such as the $C_{12}$-$C_{18}$ N-methyl glucamides, as described for example in WO 92 06154 and U.S. Pat. No. 5,194,639, and the N-alkoxy polyhydroxy fatty acid amides, such as $C_{10}$-$C_{18}$ N-(3-methoxypropyl) glucamide.

Additional non-limiting examples of cleansing surfactants may include amphoteric or zwitterionic cleansing surfactants including; alkyl amine oxides, alkyl betaines, alkyl amidopropyl betaines, alkyl sulphobetaines (sultaines), alkyl glycinates, alkyl carboxyglycinates, alkyl amphoacetates, alkyl amphopropionates, alkylamphoglycinates, alkyl hydroxy sultaines, alkyl amidopropyl hydroxysultaines, acyl taurates and acyl glutamates, wherein the alkyl and acyl groups have from 8 to 19 carbon atoms.

Preferably, the cleansing surfactant is selected from the group consisting of sodium lauryl sulphate, sodium lauryl ether sulphate (n)EO, (where n is from 1 to 3), sodium ($C_{12-13}$) pareth sulphate, ammonium lauryl sulphate, ammonium lauryl ether sulphate(n)EO, (where n is from 1 to 3), alpha olefin sulfonate (of general formula $R^1$—CH=CH—$SO_3^-M^+$, in which $R^1$ is selected from linear or branched alkyl groups having from 14 to 16 carbon atoms and mixtures thereof; and M is a solubilizing cation), lauyl taurate, cocyl taurate, sodium cocoyl isethionate, lauryl ether carboxylic acid, lauryl betaine, coco betaine, cocamidopropyl betaine, sodium cocoamphoacetate, sodium laurylamphoacetate, lauryl hydroxy sultaine, coco hydroxy sultaine, lauryl aminopropyl hydroxy sultaine, coco aminopropyl hydroxy sultaine, and mixtures thereof.

Preferably, mixtures of any of the anionic, non-ionic and amphoteric cleansing surfactants has a ratio of primary to secondary surfactant of between 1:1-10:1, more preferably 2:1-9:1 and most preferably 3:1-8:1, based on the inclusion weight of the cleansing surfactant in the hair cleansing composition.

Preferably, the hair cleansing composition of the present invention comprises from 1 to 50%, preferably from 2 to 40%, more preferably from 4 to 25% of total surfactant, based on the total weight of the composition.

The aqueous composition of the present invention preferably has a pH from 3 to <7 (for example 3 to 6.5), preferably 3.5 to <7, more preferably 3.8 to 6.5.

Optionally, a hair cleansing composition for use in the invention may contain further ingredients, (non-limiting examples of which are described below) to enhance performance and/or consumer acceptability.

Silicones

Optionally, hair cleansing compositions of the invention may comprise, emulsified droplets of a silicone conditioning agent, for enhancing conditioning performance. The emulsified silicone is preferably selected from the group consisting of polydiorganosiloxanes, silicone gums, amino functional silicones and mixtures thereof.

Suitable silicones include polydiorganosiloxanes, in particular polydimethylsiloxanes which have the CTFA designation dimethicone. Also suitable for use compositions of the invention (particularly shampoos and conditioners) are polydimethyl siloxanes having hydroxyl end groups, which have the CTFA designation dimethiconol. Also suitable for use in compositions of the invention are silicone gums having a slight degree of cross-linking, as are described for example in WO 96/31188.

The viscosity of the emulsified silicone itself (not the emulsion or the final hair conditioning composition) is typically at least 10,000 cst at 25° C. the viscosity of the silicone itself is preferably at least 60,000 cst, most preferably at least 500,000 cst, ideally at least 1,000,000 cst. Preferably the viscosity does not exceed $10^9$ cst for ease of formulation.

Emulsified silicones for use in the hair cleansing compositions of the invention will typically have a D90 silicone droplet size in the composition of less than 30, preferably less than 20, more preferably less than 10 micron, ideally from 0.01 to 1 micron. Silicone emulsions having an average silicone droplet size (D50) of 0.15 micron are generally termed microemulsions.

Silicone particle size may be measured by means of a laser light scattering technique, for example using a 2600D Particle Sizer from Malvern Instruments. Examples of suitable pre-formed emulsions include Xiameter MEM 1785 and microemulsion DC2-1865 available from Dow Corning. These are emulsions/microemulsions of dimethiconol. Cross-linked silicone gums are also available in a pre-emulsified form, which is advantageous for ease of formulation.

A further preferred class of silicones for inclusion in hair cleansing compositions of the invention are amino functional silicones. By "amino functional silicone" is meant a silicone containing at least one primary, secondary or tertiary amine group, or a quaternary ammonium group. Examples of suitable amino functional silicones include: polysiloxanes having the CTFA designation "amodimethicone".

Specific examples of amino functional silicones suitable for use in the invention are the aminosilicone oils DC2-8220, DC2-8166 and DC2-8566 (all ex Dow Corning).

Suitable quaternary silicone polymers are described in EP-A-0 530 974. A preferred quaternary silicone polymer is K3474, ex Goldschmidt.

Also suitable are emulsions of amino functional silicone oils with non ionic and/or cationic surfactant.

Pre-formed emulsions of amino functional silicone are also available from suppliers of silicone oils such as Dow Corning and General Electric. Specific examples include DC939 Cationic Emulsion and the non-ionic emulsions DC2-7224, DC2-8467, DC2-8177 and DC2-8154 (all ex Dow Corning).

The total amount of silicone is preferably from 0.01 wt % to 10% wt of the total hair cleansing composition more preferably from 0.1 wt % to 5 wt %, most preferably 0.5 wt % to 3 wt % is a suitable level.

Cationic Polymers

Optionally, the hair cleansing compositions of the present invention may include cationic polymers for enhancing conditioning performance.

Suitable cationic polymers may be homopolymers which are cationically substituted or may be formed from two or more types of monomers. The weight average ($M_w$) molecular weight of the polymers will generally be between 100 000 and 3 million daltons. The polymers will have cationic nitrogen containing groups such as quaternary ammonium or protonated amino groups, or a mixture thereof. If the molecular weight of the polymer is too low, then the conditioning effect is poor. If too high, then there may be problems of high extensional viscosity leading to stringiness of the composition when it is poured.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give polymers having a cationic charge density in the required range, which is generally from 0.2 to 3.0 meq/gm. The cationic charge density of the polymer is suitably determined via the Kjeldahl method as described in the US Pharmacopoeia under chemical tests for nitrogen determination.

Suitable cationic polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1-C7 alkyl groups, more preferably C1-3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerised in the amine form and then converted to ammonium by quaternization.

The cationic polymers can comprise mixtures of monomer units derived from amine- and/or quaternary ammonium-substituted monomer and/or compatible spacer monomers.

Suitable (non-limiting examples of) cationic polymers include:

cationic diallyl quaternary ammonium-containing polymers including, for example, dimethyldiallylammonium chloride homopolymer and copolymers of acrylamide and dimethyldiallylammonium chloride, referred to in the industry (CTFA) as Polyquaternium 6 and Polyquaternium 7, respectively;

mineral acid salts of amino-alkyl esters of homo- and co-polymers of unsaturated carboxylic acids having from 3 to 5 carbon atoms, (as described in U.S. Pat. No. 4,009,256);

cationic polyacrylamides (as described in WO95/22311).

Other cationic polymers that can be used include cationic polysaccharide polymers, such as cationic cellulose derivatives, cationic starch derivatives, and cationic guar gum derivatives.

Cationic polysaccharide polymers suitable for use in compositions for use in the invention include monomers of the formula:

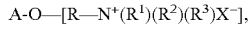

A-O—[R—N$^+$(R$^1$)(R$^2$)(R$^3$)X$^-$], wherein: A is an anhydroglucose residual group, such as a starch or cellulose anhydroglucose residual. R is an alkylene, oxyalkylene, polyoxyalkylene, or hydroxyalkylene group, or combination thereof. R$^1$, R$^2$ and R$^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in R$^1$, R$^2$ and R$^3$) is preferably about 20 or less, and X is an anionic counterion.

Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from the Amerchol Corporation, for instance under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581). Examples of such materials include the polymer LR and JR series from Dow, generally referred to in the industry (CTFA) as Polyquaternium 10.

A particularly suitable type of cationic polysaccharide polymer that can be used is a cationic guar gum derivative, such as guar hydroxypropyltrimethylammonium chloride (commercially available from Rhodia in their JAGUAR trademark series). Examples of such materials are JAGUAR C13S, JAGUAR C14 and JAGUAR C17.

Mixtures of any of the above cationic polymers may be used.

Cationic polymer may be present in a hair cleansing composition for use in the invention at levels of from 0.01 to 5%, preferably from 0.02 to 1%, more preferably from 0.05 to 0.8% by total weight of cationic polymer based on the total weight of the composition.

Additional Ingredients

The hair cleansing composition for use in the invention may further comprise additional optional ingredients for enhancing performance and/or consumer acceptability, preferably selected from the group consisting of at least one of an antibacterial agent, an anti-dandruff agents, a foam booster, a perfume, encapsulates (for example encapsulated fragrance) a dye, a colouring agent, a pigment, a preservative, a thickener, a protein, a phosphate ester, a buffering agent, a pH adjusting agent, an opacifier, a viscosity modifier, an emollient, a sunscreen, an emulsifier, a sensate active (for example menthol and menthol derivatives), vitamins, mineral oils, essential oils, lipids, natural actives, glycerine, natural hair nutrients such as botanicals, fruit extracts, sugar derivatives and amino acids, microcrystalline cellulose and mixtures thereof.

Preferably, the hair cleansing composition of the present invention includes from 0.01 to 20 wt % of the optional ingredient, more preferably from 0.05 to 10 wt %, still more preferably from 0.075 to 7.5 wt % and most preferably, from 0.1 to 5 wt % of the at least one cosmetic ingredient, by weight of the total composition.

Where the hair cleansing composition of the invention is an antidandruff shampoo, it comprises an antidandruff agent.

Antidandruff agents are compounds that are active against dandruff and are typically antimicrobial agents, preferably antifungal agents. Antidandruff agents typically display a minimum inhibitory concentration of about 50 mg/ml or less against *Malassezia*.

The total amount of anti-dandruff agent is preferably present at levels of from 0.01% to 30% by weight, more preferably 0.05% to 10%, even more preferably 0.1% to 5% and most preferably 0.2% to 4% by weight of the total hair cleansing composition.

The antidandruff agent is preferably selected from metal pyrithiones, azoles, octopirox (piroctone olamine), selenium sulfide, salicylic acid and combinations thereof, preferably metal pyrithiones, azoles and octopirox, and mixtures thereof.

Suitable metal pyrithiones include zinc pyrithione, copper pyrithione, silver pyrithione, zirconium pyrithione, and mixtures thereof. The most preferred metal pyrithione is zinc pyrithione.

Where the anti-dandruff agent is zinc pyrithione, preferred levels in hair cleansing compositions of the invention are from 0.1 to 3%, more preferably from 0.2 to 2%, most preferably from 0.5 to 1.5%, by weight based on the total weight of the composition. The particles of zinc pyrithione may be amorphous or may take various regular or irregular crystalline forms such as rods, needles, blocks, platelets and mixtures thereof. The average particle diameter of the zinc pyrithione particles (maximum dimension) is typically from about 0.1 to about 50 μm, preferably from about 0.1 m to about 10 μm, more preferably from about 0.1 μm to about 5 μm as determined, for example, using a Horiba LA-910 Laser scattering particle size distribution analyzer.

Azole based antifungal agents include ketoconazole and climbazole, preferably climbazole.

Other suitable antidandruff agents are octopirox (piroctone olamine), selenium sulfide and salicylic acid.

Suspended Particles

The compositions of the invention preferably contain suspended particles. The particles provide a benefit such as visual appearance, fragrance, antidandruff, lubrication and so on.

The suspended particles are preferably selected from silicone droplets, petrolatum jelly, in-soluble anti-dandruff agents, appearance modifiers (pearlescers) and microcapsules.

A pearlescer may be included to improve visual appearance and/or consumer appeal of the product. Preferably the pearlescer is selected from mica, titanium dioxide, titanium dioxide coated mica, glycol distearate, and mixtures thereof.

The suspended particle may be a microcapsule. The benefit agent of the core of the microcapsule may suitably be selected from perfumes, cosmetic active ingredients such as antimicrobial agents, antidandruff agents, moisturisers, conditioning agents, sunscreening agents, physiological coolants and emollient oils; and mixtures thereof.

The term "benefit agent" in the context of this invention includes materials which can provide a benefit to the hair and/or the scalp as well as those materials which are beneficially incorporated into personal cleansing compositions, such as aesthetic agents.

The polymeric shell of the microcapsule may be prepared using methods known to those skilled in the art such as coacervation, interfacial polymerisation and polycondensation.

The process of coacervation typically involves encapsulation of a generally water-insoluble material by the precipitation of colloidal material(s) onto the surface of droplets of the material. Coacervation may be simple e.g. using one colloid such as gelatin, or complex where two or possibly more colloids of opposite charge, such as gelatin and gum arabic or gelatin and carboxymethyl cellulose, are used under carefully controlled conditions of pH, temperature and concentration.

Interfacial polymerisation produces encapsulated shells from the reaction of at least one oil-soluble wall forming material present in the oil phase with at least one water-soluble wall forming material present in the aqueous phase. A polymerisation reaction between the two wall-forming materials occurs resulting in the formation of covalent bonds at the interface of the oil and aqueous phases to form the capsule wall. An example of a shell capsule produced by this method is a polyurethane capsule.

Polycondensation involves forming a dispersion or emulsion of water-insoluble material (e.g. perfume) in an aqueous solution of precondensate of polymeric materials under appropriate conditions of agitation to produce capsules of a desired size, and adjusting the reaction conditions to cause condensation of the precondensate by acid catalysis, resulting in the condensate separating from solution and surrounding the dispersed water-insoluble material to produce a coherent film and the desired microcapsules.

A preferred method for forming microcapsules for use in the invention is polycondensation, typically to produce aminoplast encapsulates. Aminoplast resins are the reaction products of one or more amines with one or more aldehydes.

Examples of suitable amines include urea, thiourea, melamine and its derivatives, benzoguanamine and acetoguanamine and combinations of amines.

Preferably the polymeric shell of the microcapsule is an aminoplast resin selected from melamine formaldehyde, urea formaldehyde, melamine glyoxal and polyurea formed by reaction of polyisocyanates and polyamines. The most preferred polymeric shell is selected from melamine glyoxal and polyurea.

Advantageously the polymeric shell comprises at most 20 wt % of the weight of the microcapsules.

By modifying process conditions microcapsules of a desired size can be produced in known manner. The microcapsules typically have a mean diameter in the range 1 to 500 microns, preferably 1 to 300 microns, more preferably 1 to 50 microns and most preferably 1 to 10 microns. If necessary, the microcapsules as initially produced may be filtered or screened to produce a product of greater size uniformity.

In a typical composition according to the invention the level of microcapsules (iii) will generally range from 0.2 to 2%, and preferably ranges from 0.5 to 1.5% by weight based on the total weight of the composition.

Perfume encapsulates are a preferred type of microcapsule suitable for use in the present invention.

The hair cleansing composition is preferably a hair shampoo composition. During use, the composition is typically rinsed off with water.

The invention is now illustrated by the following non-limiting examples.

EXAMPLES

Materials

The materials and compositions used are detailed in table 3.

TABLE 3

Compositions of comparative materials and materials according to the present invention used in examples

|  | Polyol:fibre ratio | Polyol |
|---|---|---|
| Comparative Example A | 0:1 | None |
| Example 1 | 1:4 | Glycerol |
| Example 2 | 1:2.5 | Glycerol |
| Example 3 | 1:2.5 | Sucrose |
| Example 4 | 1:2.5 | Sorbitol |

Method for Making a Composition According to the Invention (Examples 1 to 2)

Step (1) Water was added to de-pectinized citrus peel to obtain an aqueous slurry having a dry substance content of about 4 wt %. The slurry was one time charged to a pressure homogenizer (APV homogenizer, Rannie 15-20.56) at 600 bars. An aqueous slurry containing citrus fibers was obtained.

Step (2) A precipitation tank was filled with an aqueous isopropanol solution (about 82 wt % isopropanol in water). The aqueous slurry containing citrus fibers was brought under agitation into the precipitation tank by using a volumetric pump and a precipitate in the form of granules having sizes between 5 mm and 50 mm was formed in the tank. The slurry:isopropanol ratio was 1:2. Agitation by stirring was provided while bringing said slurry into the tank and the precipitate was kept in the tank for about 30 minutes.

Step (3) The precipitate was charged to a centrifuge decanter (Flottweg centrifuge) operated at above 4000 rpm, to separate the liquid phase (i.e. water and isopropanol) from the citrus fibers.

Step (4) Steps (2) and (3) were repeated and the precipitate was subjected to an extraction step to increase the dry substance content. The extraction step was carried out by feeding the precipitate to a screw press. The speed and pressure of the press were adjusted to obtain a semi-dry cake having a dry substance content of about 22 wt. %.

Step (5) The semi-dry cake was comminuted using a Lodige type FM 300 DMZ mixer, for about 15 to 30 minutes, to obtain grains having sizes in the range of 1 millimeter. The comminuted semi-dry cake was mixed with commercial glycerol in a glycerol:fiber ratio of 1:4 (Example 1) and 1:2.5 (Example 2)

Step (6) The comminuted cake was dried in a ventilated oven at 40 degrees Celsius for about 2 hours to reach a moisture content of about 8 wt. %.

Method for a Composition not According to the Invention (Examples 3 and 4)

The compositions were made according to Example 2, with the difference that at step 5 instead of glycerol, sucrose or sorbitol were used. In particular for Example 3 sucrose was used in a sucrose:fiber ratio of 1:2.5. For Example 4 sorbitol was used in a sorbitol:fiber ratio of 1:2.5.

Method for Making Hair Cleansing Products

Hair cleansing products were made having a formulation as set out in table 4. The process used to manufacture the hair cleansing products is further described below.

TABLE 4

Hair cleansing product formulations (amounts are based on wt. % unless otherwise indicated).

| | Hair Cleansing Product | | |
|---|---|---|---|
| | Hair Product A1 & C1 | Hair Product B1 | Hair Products B2, B3, B4 |
| | Composition(s) Used* | | |
| Ingredient | Comparative Example A Inclusion Level wt. % | Example 1 Inclusion Level wt. % | Examples 2, 3 and 4 Inclusion Level wt. % |
| Composition** | 0.2 | 0.25 | 0.28 |
| Sodium Laureth Sulphate | 12 | 12 | 12 |
| Cocoamidopropyl Betaine | 1.6 | 1.6 | 1.6 |
| Guar Hydroxypropyltrimonium Chloride | 0.2 | 0.2 | 0.2 |
| Mica (titanium dioxide | 0.2 | 0.2 | 0.2 |
| Conditioning agents | 2.54 | 2.54 | 2.54 |
| Preservative | 0.16 | 0.16 | 0.16 |
| Sodium Chloride | 1.10 | 1.10 | 1.10 |
| Fragrance | 0.65 | 0.65 | 0.65 |
| Water | to balance | to balance | to balance |

*The composition refers to examples of the composition listed in table 3
**Composition as according to Example 1-4 or Comparative Example A For Hair Cleansing Products A1 and B1-B4:

As a first step, a coarse premix was prepared of the composition (as according to Example 1, 2, 3, 4 or Comparative Example A) and water, comprising a total of 10 wt. % of the product formulation (part of the water-phase was used for this purpose). The premix was stirred using a paddle mixer operated at 200 rpm for 15 minutes ensuring that clumping did not occur.

The remaining available water in the product was charged to a 50 litre process vessel and the coarse premix of the composition and water was injected in-line at a rate of 15 kg/hr into the recirculation loop of the process vessel just upstream of a 150/250 Silverson rotor stator mill operating at a tip speed of 24 m/s. The mixture was continually recirculated via Silverson rotor stator mill for 60 minutes at a flow rate of 250 kg/hr. The mill was then switched off and the remaining ingredients were added via the standard methods of addition known in the art to produce a product with a viscosity specification of 4000-6000 cP (RV5, 20 rpm, 30° C., 1 minute) and pH specification of 5.5-6.5
For Hair Cleansing Products C1:

Water was added to de-pectinized citrus peel to obtain an aqueous slurry having a dry substance content of about 2 wt %. The slurry was one time charged to a pressure homogenizer (APV homogenizer, Rannie 15-20.56) at 500 bars. An aqueous slurry containing citrus fibers was obtained. The remaining available water in the product was charged to a 50 litre process vessel and the 2% aqueous slurry was injected in-line at a rate of 15 kg/hr into the recirculation loop of the process vessel just upstream of a 150/250 Silverson rotor stator mill operating at a tip speed of 24 m/s. The mixture was continually recirculated via Silverson rotor stator mill for 60 minutes at a flow rate of 250 kg/hr. The mill was then switched off and the remaining ingredients were added via the standard methods of addition known in the art to produce a product with a viscosity specification of 4000-6000 cP (RV5, 20 rpm, 30° C., 1 minute) and pH specification of 5.5-6.5.

Shear Profile Analysis of the Hair Cleansing Products

Rheology flow curves were subsequently generated for the final hair cleansing products using the following two-step protocol.

The instrument used was a Thermo Scientific RS1 (Rheostress 1) with Z20 DIN, profiled DIN concentric cylinder geometry. The measurement was conducted at two temperatures; 25° C. and 50° C.

Step 1—Controlled stress steps from 0.01 to 400 Pa; 40 steps logarithmically spaced in stress with 40 seconds being spent at each point to measure the shear rate (and hence viscosity); Step 1 is terminated once a shear rate of 0.1 $s^{-1}$ is reached.

Step 2—Controlled shear rate steps from 0.1 to 1200 $s^{-1}$; 40 steps logarithmically spaced in shear rate with 6 seconds being spent at each point to determine the stress required to maintain the shear rate and hence the viscosity.

The results of the first two steps are combined being careful to remove any overlap and to ensure that the required shear rates were achieved at the start of the step.

The yield stress in Pascals (Pa) is then taken to be the value of the stress at a shear rate of 0.1 $s^{-1}$, that is, the equivalent of the y-axis intercept in a Herschel-Buckley plot of shear stress versus shear rate. The results are given in Table 5.

TABLE 5

Yield stress of hair cleansing products containing Examples 1-4 (Ex. 1-4) and Comparative Example A (Comp A) compositions

| | Hair Cleansing Product | | | | | |
|---|---|---|---|---|---|---|
| | Hair Product A1 | Hair Product B1 | Hair Product B2 | Hair Product B3 | Hair Product B4 | Hair Product C1 |
| | Composition included in Hair cleansing product | | | | | |
| | Comp A | Ex. 1 | Ex. 2 | Ex. 3 | Ex. 4 | Comp A |
| [1] Additive | None | Glycerol | Glycerol | Sucrose | Sorbitol | None |
| [2] Ratio | 0:1 | 1:4 | 1:2.5 | 1:2.5 | 1:2.5 | 0:1 |
| Inclusion level of composition in product | 0.2 | 0.25 | 0.28 | 0.28 | 0.28 | 0.2 |
| [3] Level of citrus fibers in product | 0.2 | 0.2 | 0.2 | 0.2 | 0.2 | 0.2 |
| Yield Stress (Pa) 25° C. | 1.43 | 3.23 | 2.58 | 2.67 | 2.80 | 2.47 |
| Yield Stress (Pa) 50° C. | 0.32 | 1.81 | 1.25 | 1.37 | 1.59 | 1.24 |

[1] The type of ingredient distributed between the fibrils of the used composition.
[2] The ratio of the ingredient to the dry weight of the primary cell wall material in the used composition.
[3] The amount of defibrillated primary cell wall material comprising cellulose microfibrils in the hair cleansing product, by weight of total composition.

When hair cleansing products are prepared using the same low shear process, the yield stress measurements of hair cleansing products comprising compositions of the present invention (B1-B4) are greater than that of the hair cleansing product prepared using Comparative Example A (A1).

Hair cleansing products, prepared under low shear, using compositions according to the present invention (B1-B4) have comparable yield stress measurements to the hair cleansing product with Comparative Example A, where high energy treatment with a high pressure homogeniser has been used (C1). This highlights the benefit delivered by the compositions according to the present invention in enabling use of a low shear process to deliver hair cleansing products with higher yield stresses.

A higher hair cleansing product yield stress gives greater suspending capability and infers improved stability of the hair cleansing product.

The invention claimed is:
1. A hair cleansing composition comprising:
a) from 1 to 50 wt % of a cleansing surfactant selected from the group consisting of anionic surfactant, zwitterionic or amphoteric surfactant, non-ionic surfactant and mixtures thereof; and b) from 0.01 to 3 wt %, by weight of the total composition, of defibrillated primary cell wall material comprising cellulose microfibrils, wherein the defibrillated primary cell wall material comprises up to 20 wt. % water, based on the total weight of the fibrils;

wherein the cellulose has an average degree of crystallinity of less than 50%, the defibrillated primary cell wall material comprises polyol distributed between the fibrils, and the polyol is selected from glycerol, diglycerol, monopropylene glycol, dipropylene glycol, ethylene glycol and polyethylene glycol, sorbitol, sucrose and mixtures thereof.

2. The composition according to claim 1, wherein the defibrillated primary cell wall material comprises up to 15 wt. % water, based on the total weight of the fibrils.

3. The composition according to claim 1, wherein the composition is a hair shampoo.

4. The composition according to claim 1, wherein the primary cell wall material comprises at least 50 wt. % of cellulose microfibrils, based on the total dry weight of the primary cell wall material.

5. The composition according to claim 1, wherein the cellulose microfibrils have an average degree of crystallinity of up to 40%.

6. The composition according to claim 1, wherein the total amount of polyols, including polyol distributed between the fibres and any optional additional polyol, in the hair cleansing composition is at least 10 wt. %, based on the dry-weight of the primary cell wall material in the final composition.

7. The composition according to claim 1, wherein the defibrillated primary cell wall material comprising cellulose microfibrils is present in an amount of from 0.02 to 2 wt % by weight of the total composition.

8. The composition according to claim 1, wherein the microfibrils are citrus fibres.

9. The composition according to claim 1, wherein the fibres are activated citrus fibers having a self-suspending capacity of 45-58% and a G' of between 600-1200 Pa;

wherein the self-suspending capacity is determined, in the presence of glycerol, at 0.1 wt % dry fibre upon dispersion at 8000 rpm for 10 minutes; and wherein G' is determined in the presence of the glycerol, at 2.0 wt % dry fibre dispersed at 8000 rpm for 10 minutes and between 10-40 wt % glycerol.

10. The composition according to claim 1, wherein the polyol is glycerol present in an amount of from 10 to 40 wt %, based on the weight of the dry fibres.

11. A method of cleansing hair comprising the step of applying to the hair, the cleansing composition of claim 1.

12. A process for the manufacture of a hair cleansing composition comprising the steps of:

a) providing a defibrillated primary cell wall material comprising cellulose microfibrils, wherein the defibrillated primary cell wall material comprises up to 20 wt. % water, based on the total weight of the fibrils; and wherein the cellulose has an average degree of crystallinity of less than 50%, the defibrillated primary cell wall material comprises polyol distributed between the fibrils, and the polyol is selected from glycerol, diglycerol, monopropylene glycol, dipropylene glycol, ethylene glycol and polyethylene glycol, sorbitol, sucrose and mixtures thereof;

b) providing further ingredients comprising at least a water-phase and from 1 to 50 wt % of a cleansing surfactant selected from the group consisting of anionic surfactant, zwitterionic or amphoteric surfactant, nonionic and mixtures thereof;

c) mixing the ingredients provided at step a) and b) under low shear to provide a cleaning product, where mixing under low-shear includes using a rotor stator mixer or dispersion disc mixer with a rotor or disc tip speed of less than 40 m/s.

13. The composition according to claim 2, wherein the defibrillated primary cell wall material comprises up to 10 wt. % water, based on the total weight of the fibrils.

14. The composition according to claim 4, wherein the primary cell wall material comprises at least 70 wt. % of cellulose microfibrils, based on the total dry weight of the primary cell wall material.

15. The composition according to claim 5, wherein the cellulose microfibrils have an average degree of crystallinity of up to 35%.

16. The composition according to claim 6, the total amount of polyols, including polyol distributed between the fibres and any optional additional polyol, in the hair cleansing composition is 15 to 1000 wt % based on the dry-weight of the primary cell wall material in the final composition.

17. The composition according to claim 16, the total amount of polyols, including polyol distributed between the fibres and any optional additional polyol, in the hair cleansing composition is 20 to 500 wt. % based on the dry-weight of the primary cell wall material in the final composition.

18. The composition according to claim 7, wherein the defibrillated primary cell wall material comprising cellulose microfibrils is present in an amount of from 0.05 to 1.5 wt % by weight of the total composition.

19. The process according to claim 12, wherein the rotor stator mixer or dispersion disc mixer has a rotor or disc tip speed of from 5 to 35 m/s.

* * * * *